United States Patent [19]

Dasgupta

[11] Patent Number: 5,316,630
[45] Date of Patent: May 31, 1994

[54] METHODS FOR CHROMATOGRAPHY ANALYSIS

[75] Inventor: Purnendu K. Dasgupta, Lubbock, Tex.

[73] Assignee: Dionex Corporation, Sunnyvale, Calif.

[21] Appl. No.: 40,014

[22] Filed: Mar. 30, 1993

[51] Int. Cl.$^5$ .............. G01N 27/26; G01N 27/447; G01N 30; G01N 02; B01D 15/08

[52] U.S. Cl. .............. 204/180; 204/299.00 R; 73/61.52; 73/61.58; 210/198.2; 210/656; 422/70

[58] Field of Search .......... 204/180.1, 299 R; 73/61.58, 61.52; 210/198.2, 656; 422/70

[56] References Cited

U.S. PATENT DOCUMENTS

| | | | |
|---|---|---|---|
| 3,590,628 | 7/1971 | Orr | 73/23.23 |
| 3,897,213 | 7/1975 | Stevens | 422/81 |
| 3,920,397 | 11/1975 | Small | 436/79 |
| 3,925,019 | 12/1975 | Small | 436/79 |
| 3,926,559 | 12/1975 | Stevens | 436/79 |
| 4,459,357 | 7/1984 | Jansen | 436/161 |
| 4,474,664 | 10/1984 | Stevens | 210/656 |
| 4,533,518 | 8/1985 | Hanaoka et al. | 422/70 |
| 4,579,663 | 4/1986 | Poile et al. | 210/656 |
| 4,751,004 | 6/1988 | Stevens | 210/659 |
| 4,988,447 | 1/1991 | Hellinger | 210/659 |
| 4,999,098 | 3/1991 | Pohl | 204/301 |
| 5,234,586 | 8/1993 | Afeyan et al. | 210/198.2 |

OTHER PUBLICATIONS

Gross et al. Anal. Chem. 62:427–431 (1990).
Bachmann et al. Journal of Chrom. 626:259–265 (1992).
Gross et al. Journal of Chrom. 480:169–178 (1989).
Foret et al. Journal of Chrom. 470:299–308 (1989).
Foret et al. Electrophoresis 11:780–783 (1990).
Henshall et al. Journal of Chrom. 608:413–419 (1992).
Haddad, P. R., et al. Ion Chromatography: Principles and Applications, Elsevier Science Publishing Co. p. 263 (1990).
Gjerde, D. T. et al. Ion Chromatography, Alfred Huthig Verlag, p. 127 (1987).
Johnson, E. L. Ion Chromatography, Marcel Dekker Inc., Tarter J. G. Ed. pp. 5–6 (1987).
Stillian, John, Liquid Chromatography, Sep. 1985.

*Primary Examiner*—John Niebling
*Assistant Examiner*—John S. Starsiak, Jr.
*Attorney, Agent, or Firm*—Flehr, Hohbach, Test, Albritton & Herbert

[57] ABSTRACT

A method is described for the normalization and standardization of variabilities of electropherograms obtained with conductometric capillary electrophoresis. The variabilities may be associated with differences in the sample injection volume between two or more runs. Alternatively, the variabilities may be associated with alterations in the electroosmotic flow velocity of two or more runs.

26 Claims, 3 Drawing Sheets

METHODS FOR CHROMATOGRAPHY ANALYSIS

FIELD OF THE INVENTION

The present invention relates to a method for the standardization of chromatograms obtained in chromatography systems. The present invention may be particularly useful in capillary electrophoresis systems.

BACKGROUND OF THE INVENTION

Capillary electrophoresis (CE) is an electrophoresis technique utilizing small bore capillaries. CE provides methods for the separation of ionic species including macromolecules. The efficiency of CE can be relatively high, i.e. in excess of 400,000 theoretical plates, and thus is being explored for a number of different applications.

A typical CE system includes a 50-100 micrometer internal diameter silica capillary tube filled with a suitable electrically conducting buffer. The outlet end of the capillary is immersed in a reservoir containing the buffer and an electrode. A sample containing ions of interest is introduced into the inlet end of the capillary and then the inlet is placed in another reservoir containing the buffer and another electrode. Since a small diameter capillary is used in CE, a relatively high applied voltage can be used without the generation of thermal gradients in the capillary; thus the electrodes are connected to a power supply capable of delivering ~30 kV per 100 cm of capillary. A detector is placed between the two electrodes to permit detection of various ionic species migrating in the capillary. A detector so positioned is often referred to as an on-column detector. Typically, an integrator is attached to the detector, such that the peak areas may be measured.

The movement of the sample ions of interest is controlled by two factors: the electrophoretic velocity and the electroosmotic flow velocity. The total migration velocity is the vector sum of these two terms.

Electrophoretic migration is the migration of the sample ion towards the oppositely charged electrode under the influence of the electric field. The electrophoretic mobility of any particular ion is the electrophoretic velocity per unit field strength.

Electroosmotic flow (EOF) is the bulk flow of the buffer in the capillary. EOF is due to the charge of the inside surface of the capillary which is in contact with buffer containing mobile counterions. For example, an unmodified silica capillary surface comprises silanol (Si—OH) groups that are negatively charged (Si—O$^-$) when the pH of the buffer is greater than about 2, and positively charged (Si—OH$_2$+) when the pH is less than about 2. Alternatively, hydrophobic cations may be adsorbed onto the inside surface of the capillary to obtain a positively charged surface at higher pHs.

When the surface is negatively charged, then the mobile counterions, for example, sodium ions (Na$^+$), migrate under the influence of the electric field and in the process drag the bulk solvent with them. Thus the direction of the electroosmotic flow is from the positive to the negative electrode when the surface is negatively charged.

When the surface is positively charged, then the mobile counterions of the positively charged surface, e.g. biphosphate ions (HPO$_4^{2-}$), migrate under the influence of the electric field and in the process drag the bulk solvent with them. Thus the direction of the electroosmotic flow is from the negative to the positive electrode when the surface is positively charged.

When the surface is not charged, then there is no electroosmotic flow, and any movement of analyte ions is due solely to electrophoretic mobility.

Thus, depending on the charge of the ions of interest, the nature and the extent of capillary surface charging and the polarity of the applied voltage, electroosmosis can augment, counteract or even override the electrophoretic movement. Since sample components to be determined must travel from the inlet end of the capillary to the detector which is located near the outlet end of the capillary, it is essential that they move in the desired direction. However, since the total migration velocity of the sample is the vector sum of the electrophoretic velocity and the electroosmotic flow velocity, it is possible that the charge of the sample is such that it would move away from the outlet electrode in the absence of electroosmotic flow; under these conditions the electroosmotic flow velocity of the bulk solution must be greater than the electrophoretic mobility of the analyte.

The detector used in the CE system is very important, and the type of detector used will usually depend on the properties of the compounds under analysis. Currently, there are a number of different detector schemes utilized in CE. These include direct and indirect photometric detection, direct and indirect fluorescence detection, as well as suppressed and non-suppressed conductometric detection. Other types of detection which may be utilized are mass spectrometry, radiometry and other electrochemical methods such as amperometry. These methods may be used either on-column or end-column, i.e. at some point after the outlet electrode.

While most organic molecules of interest display significant ultraviolet absorption such that direct photometric detection is practical, this is not the case for many inorganic ions or aliphatic carboxylic acids that display very low optical absorption. Thus indirect photometric or fluorescence detection may be utilized in these cases. For example, indirect fluorometric detection is described in Gross et al., Anal. Chem. 62:427-431 (1990); Bachmann et al., Journal of Chrom. 626:259-265 (1992); and Gross et al., Journal of Chrom. 480:169-178 (1989). Indirect photometric detection is described in Foret et al., Journal of Chrom. 470:299-308 (1989); Foret et al., Electrophoresis 11:780-783 (1990); and Henshall et al., Journal of Chrom. 608:413-419 (1992). Additionally, since electrical mobility is an intrinsic property of all ions, detection based on conductivity can be a desirable method for many uses of CE.

However, conductivity detectors are nonselective bulk property detectors. The signal arises from the difference in equivalent conductance or mobility of the charge carrier electrolyte ion and the analyte ion. In CE, a large difference in mobility of the carrier electrolyte ion and the analyte ion leads to excessive peak tailing/fronting, which means that there are practical restrictions on the choice of the eluent ion. This conflict between optimum sensitivity and separation efficiency represents the ultimate limitation of nonsuppressed conductivity detection in CE.

Electrolyte suppression, or the post run alteration of the electrolyte buffer such that the background "noise" of the buffer is decreased, has been explored for ion chromatography (see for example U.S. Pat. Nos. 3,897,213; 3,920,397; 3,925,019; 3,956,559; 4,474,664;

4,751,004; 4,459,357 and 4,999,098), and recently for CE (U.S. Ser. Nos. 07/771,336 and 07/771,597, filed Oct. 4, 1991, herein incorporated by reference). These systems are referred to as "suppressed" systems.

When conductometric detection is utilized, aspects of the electropherogram from a CE run are different from an optically detected CE run. These phenomena are the subject of the present invention.

One problem with CE is that the sample volume introduced into the capillary may vary; samples are not easily injected onto the column by a fixed volume valve. This can be a problem in other chromatography systems as well, although many systems do employ a fixed volume valve. Instead, in CE, the samples are introduced into the capillary in several ways. Typical injection modes for CE are pressurization of the sample- or standard-containing vial for a fixed length of time (pressure injection), or the application of an electrical field for a fixed length of time (electrostatic injection). Thus CE sample injection methods are based on time of injection. This means that small variabilities in time, sample viscosity, pressure or hydrostatic height may result in variabilities of the sample volume injected. This may have a profound impact on the migration time and the size of the peaks.

Furthermore, these potential variabilities may make quantification of sample peaks difficult. Quantification requires that the injected volume of the sample and the injected volume of the standard be essentially exactly the same, or that the volume of each be precisely known to compensate for injected volume differences.

Another problem with CE and other systems relying on electroosmotic flow is that it is difficult to determine the electroosmotic flow velocity, and to detect any variations in this rate. For example, in CE, the electroosmotic flow velocity in a bare silica capillary can be affected by material adsorbed on the wall from the previous injection, which may alter the flow rate. Similarly, the flow rate of different capillaries may be different due to a variety of factors. The electroosmotic flow velocity will also change as a result of a change in applied voltage. Since the flow velocity will affect the migration times of the analyte peaks, i.e. total migration velocity of the analyte, this may be a serious problem. This takes on an increased significance if an integrator is used, since the integration is dependent on time; thus a decrease in the flow rate for a sample run may result in an increase in the peak area, and vice versa.

These two limitations are addressed by the present invention.

SUMMARY OF THE INVENTION

The present invention is based on the observation that when certain types of detection is utilized in CE, and other types of chromatography, a "water dip" occurs in the detector background as the water associated with the injected sample migrates through the detector. The present invention is to a method of normalizing or standardizing two or more chromatography or CE runs by using the information contained within the water dip.

Figure 2:
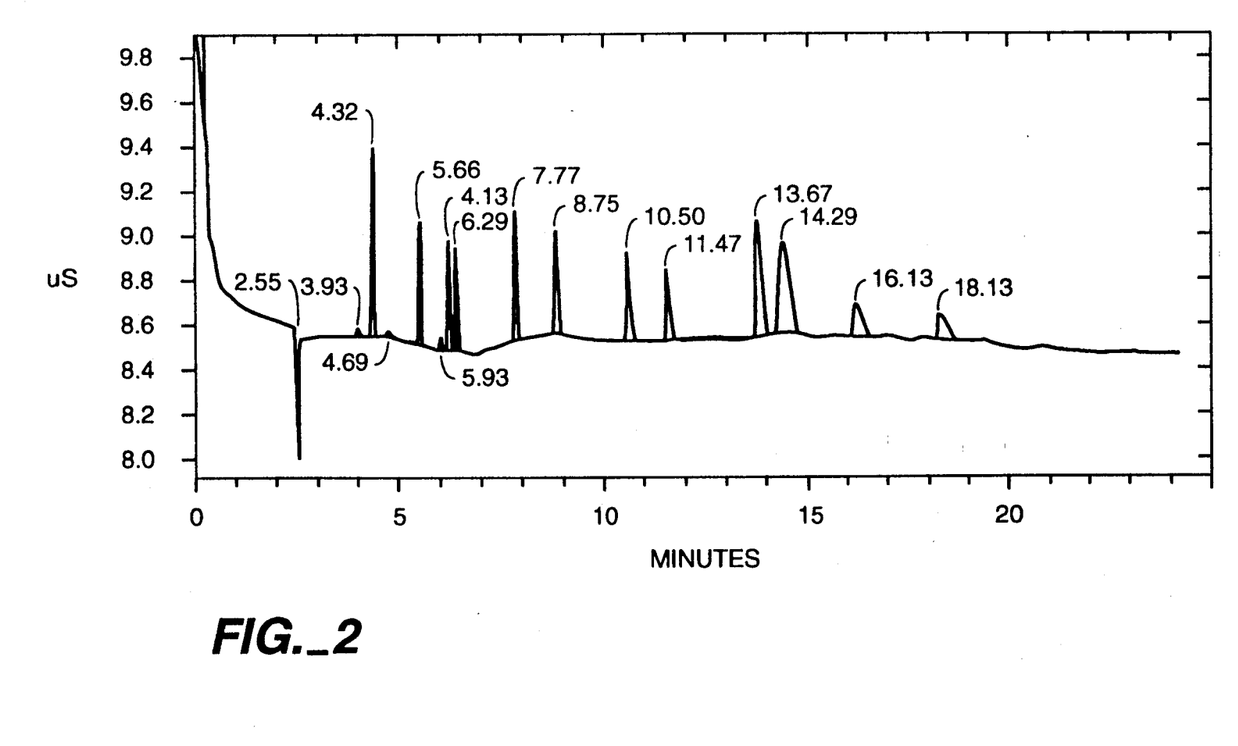
FIG. 2 depicts a standard electropherogram for the suppressed conductometric CE runs of Example 1.
Figure 3:
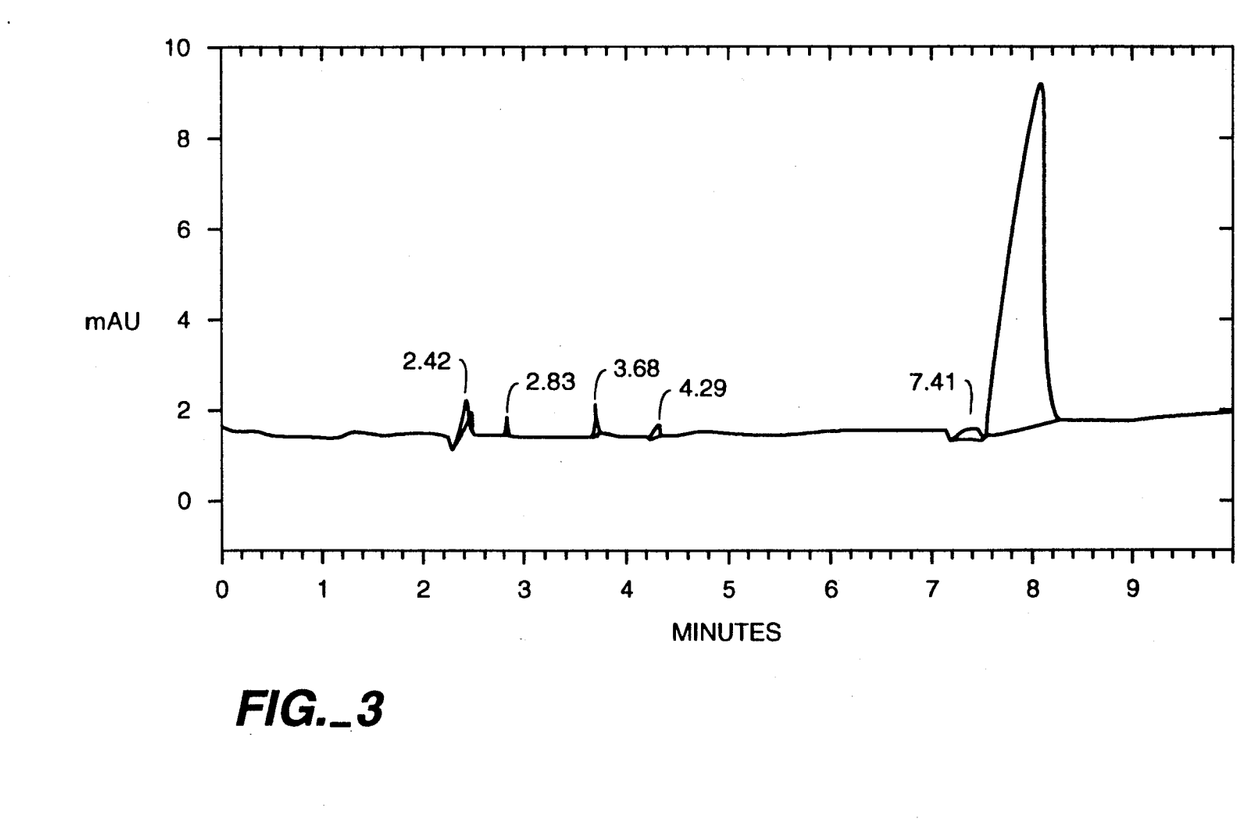
FIG. 3 depicts a standard electropherogram for CE using indirect photometric detection.

Water dips are well known in certain chromatography systems, although their significance has never been realized. For example, Stilljan, J., Liquid Chromatography, September 1985, describes an improved suppressor for ion chromatography; typical water dips may be seen in the figures, with FIG. 2 showing the interference of the water dip on quantitation at high sensitivity. These systems may use borate or carbonate eluents, and the water dips are generally of no value, since both flow rate and injection volume are known. Water dips have been shown in capillary electrophoresis as well; see for example Foret et al., J. Chrom. 470:299–308 (1989). Occasionally, the water dip may be a nuisance by interfering with accurate quantitation of early eluting peaks. For example, the water dip has been reported to hamper the analysis of early eluting peaks. See Haddad, P. R. et al., Ion Chromatography: Principles and Applications, Elsevier Science Publishing Co., page 263 (1990); Gjerde, D. T. and Fritz, J. S., Ion Chromatography, Alfred Huthig Verlag, page 127, (1987) Johnson., E. L.; Ion Chromatography, Marcel Dekker Inc., Tarter, J. G. Ed., page 5–6 (1987).

The water dip is a result of a sample being introduced onto a chromatography system when the sample diluent has a composition different from the composition of the system running buffer. When a detector is used which is capable of detecting this difference between the sample diluent and the system running buffer, the passage of the sample diluent through the detector results in a change in the detector output. Frequently, the sample diluent is such that its properties are "less" than the properties of the system running buffer. For example, in conductometric detection, ionic samples are diluted in water, and the water is less conductive than the system running buffer. This results in a "water dip" when the sample diluent water passes through the detector. In indirect photometric detection, the water of the sample has less absorbance than the system running buffer, which is typically of a high absorbance. Thus a detector response, typically negative, will result from the passage of the water through the detector cell. The same is true with indirect fluorescence detection. In direct photometric or fluorescence detection, even though the running buffer has low absorbance or fluorescence at the chosen detection conditions, often its absorbance is still greater than that of the sample diluent and a water dip is generated. It is also possible that the sample diluent will have a greater absorbance or fluorescence than the running buffer; in this case, a water peak is generated.

In capillary electrophoresis, the sample ions or other compounds are frequently in water. Since the water in the sample volume is not ionized, it moves down the capillary at the same velocity as the bulk electrolyte, as a result of the electroosmotic flow. The water associated with the sample has a lower conductivity than the bulk electrolyte and causes a dip in the detector output as it passes through the conductance cell.

The invention is based on the discovery that the information contained within the water dip is very useful in the standardization and normalization of chromatography runs, and in particular, CE runs. Applicants have discovered that there is a relationship between the area of the water dip of a standard run and the area of the water dip of a sample run, such that a comparison of these two areas will allow the correlation of the standard concentration to the sample concentration. This relationship may be determined in more than one way.

In particular, the area of the water dip is a direct measure of the injected sample volume that contained the water. In various chromatography systems, and in particular CE systems, the electroosmotic flow is of a "plug" flow nature. Thus the width of the water dip, or its area, corrected as necessary for any changes in electroosmotic flow, is a direct measure of the volume of the injected sample that contained the water. This allows comparison and quantification of the sample to the standard which has been previously difficult. This will significantly improve the precision of quantification in certain chromatography systems, and in CE systems in particular.

Therefore, included within the present invention is a method of normalizing the injection volume variabilities of chromatograms of standard runs and of sample runs. First, a chromatogram of a standard or a set of standards of known concentration is created. Then at least one chromatogram of a chromatography run of a sample or samples of interest is created. The area of the water dip for the standard run is determined, preferably through the use of an integrator attached to the detector. The area of the standard peaks or peak is also determined. Then the sample is run, and the area of the water dip of the sample run and the area of the sample peaks are determined. Then the peak areas of the sample water dip and sample components are adjusted using the formula:

Adjusted Peak Area=(measured peak area)(Area$_{wd\ std}$/Area$_{wd\ sample}$)

where Area$_{wd\ std}$ is the area of the standard run water dip and Area$_{wd\ sample}$ is the area of the sample run water dip. This calculation is done for each sample peak as well as the water dip peak of the sample run. Then the samples may be quantified using the formula:

Sample concentration=(sample adjusted peak area)(standard concentration/standard peak area).

This allows a precise determination of the concentration of a sample. Thus the standard run and the sample run or runs may be standardized or normalized for meaningful comparison.

The technique can also be used when, for example, one deliberately uses a higher sample volume to get better sensitivity relative to calibrations. It is not necessary to re-calibrate using the new sample volume or to previously know the injected volume. The same equations shown above are applied and the correct analyte concentration can be determined.

Another aspect of the present invention involves the use of the water dip as a means for the determination of the flow velocity of the system running buffer in a CE or chromatography system. The Applicants have discovered that the interval between the start of the run and the appearance of the water dip is useful in the determination of the flow velocity of system running buffer. Specifically, applicants have discovered that the relationship between the migration time of the standard run water dip and the migration time of the sample run water dip will determine any alterations in the flow velocity of the system running buffer between the two runs. Thus this relationship may be used to correlate the mobility of the standards to the mobility of the samples.

This relationship between the migration time of the water dip of the standard run and the water dip of the sample run is particularly useful in CE systems. This relationship allows the determination of any alterations in the electroosmotic flow velocity between the two runs in a number of ways, several of which are outlined below.

As outlined above, the electroosmotic flow velocity in CE may vary as a result of accumulated adsorbed material on the surface of the capillary, the introduction of a new capillary or a membrane attached to the capillary, or of a change in the applied voltage. These variations may result in a change in the migration time of the samples or standards. By calculating the time interval between the injection of the sample and the appearance of the water dip, the flow velocity for a capillary of a known volume can be determined. Once the electroosmotic flow velocity is known, the electrophoretic migration velocity may be calculated for individual standards and analytes, which is characteristic of the analyte or standard and independent of electroosmotic flow velocity, the capillary length or applied voltage. Since the electrophoretic migration velocity is a key identifying characteristic of the analyte peaks, the ability to correctly calculate the electrophoretic migration velocity through the determination of the electroosmotic flow velocity is significant.

In one aspect of the present invention, the chromatograms are normalized in the following way. First, a chromatogram is created utilizing a detector capable of reporting a change in the detector output as a result of a difference between the sample diluent and the system running buffer. This chromatogram is of a chromatography run of at least one standard of known concentration. Then at least one chromatogram of a chromatography run of a sample or samples of interest is created using the same detector. The migration times of the water dip in the standard and sample runs are determined, as well as the migration times of the standards and samples. Then the adjusted migration time is calculated according to the formula: adjusted migration time=(measured migration time)(migration time$_{wd\ std}$/migration time$_{wd\ sample}$) where migration time$_{wd\ std}$=migration time of the water dip in the standard run, and migration time$_{wd\ sample}$=migration time of the water dip in the sample run. Then sample peaks may be identified by adjusted retention time by correlating the adjusted migration times Of the samples to the adjusted migration times of the standards.

In another aspect of the present invention, electropherograms from CE are normalized in the following way. First, an electropherogram of a CE run of at least one standard of known concentration is created. Then at least one electropherogram of a CE run of a sample or samples of interest is created. The migration times of the water dip in the standard and sample runs are determined, as well as the migration time of the standards and samples. Then, the electrophoretic mobility of each of the standards and samples is calculated according to the following formula:

$$u_{ep}=L^2(1/t_s-1/t_w)/V$$

wherein
$u_{ep}$=electrophoretic mobility;
L=length of capillary;
V=applied voltage;
$t_w$=migration time of the water dip;
$t_s$=migration time of the sample.

Then the sample peaks are identified by electrophoretic mobility by correlating the electrophoretic mobility of the samples to the electrophoretic mobility of the standards.

In another aspect of the present invention, a method is described for the normalization of variabilities associated with changes in the electroosmotic flow velocity of the bulk buffer of conductometric CE in systems wherein the voltage and the capillary are not altered between the standard run and the sample runs. In these systems, the electrophoretic index of each standard and sample, which is similar to the electrophoretic mobility, may be compared or correlated.

In this aspect of the present invention, as above, the migration times of the water dips in the standard and sample runs are determined. Then the electrophoretic index is calculated according to the formula:

$$E = 1/t_s - 1/t_w$$

wherein
E = the electrophoretic index;
$t_w$ = migration time of the water dip;
$t_s$ = migration time of the sample.

Then sample peaks may be identified by the electrophoretic index by correlating or comparing the electrophoretic index of the samples to the electrophoretic index of the standards. Thus variabilities in the electroosmotic flow rate may be normalized, and meaningful comparisons made between standards and samples.

DEFINITIONS

By the term "chromatography" or grammatical equivalents herein includes a number of different chromatography methods. Chromatography can include, for example, ion exchange chromatography, ion exclusion chromatography, normal phase liquid chromatography, reversed-phase liquid chromatography (HPLC), capillary electrophoresis (CE), chromatofocusing, and micellar electokinetic capillary chromatography (MECC).

By the term "conductometric capillary electrophoresis" or grammatical equivalents herein is meant any capillary electrophoresis system which utilizes a conductivity meter as the method of peak detection. Included within the definition are both suppressed and nonsuppressed CE systems.

By the term "chromatograms" or grammatical equivalents herein is meant the time trace of a chromatography run, i.e. the time trace of the detection measurement, with peaks resulting from changes in the detector output as the samples pass through the detection cell. The term is used regardless of the method of detection. The term includes electropherograms, which are particular to CE runs. Electropherograms include CE runs utilizing conductivity detection, with peaks resulting from changes in conductivity in the sample as it passes through the conductivity meter. These peaks are the result of a difference in conductivity and the resulting detector response.

The peaks of a chromatogram or electropherogram can be negative or positive. For example, in the case of an electropherogram of a conductometric CE run, a peak may be negative in the sense it results from the sample passing through the detector being less conductive than the bulk electrolyte, (as in the case of water dips). The peaks may also be positive, when the sample passing through the conductivity meter is more conductive than the bulk electrolyte (as in the case of sample or analyte peaks).

By the term "water dip" or grammatical equivalents herein is meant the negative peak resulting from the passage of the water or sample electrolyte in which the sample was injected onto the CE system through the conductivity meter.

By the term "sample" or "analyte" or "sample compounds" or grammatical equivalents herein is meant any compound which may be run on a chromatography system for the purposes of analysis. It may be a compound whose identity is unknown, or a known compound whose concentration is unknown, or both. It may be an ion, a protein, inorganic and organic molecules, nucleic acids, and others. It is understood that the use of the singular or plural form of these words is not determinative and should not limit interpretation of the present invention and claims.

By the term "standard" or grammatical equivalents herein is meant a compound which is run on a conductometric CE system, whose identity and concentration are known. It is understood that the use of the singular or plural form of the word "standard" is not determinative and should not limit interpretation of the present invention and claims.

By the term "determining the area of the water dip or samples" or grammatical equivalents herein is meant any measurement used to determine or approximate the area under the curve of a peak on an electropherogram. One can either integrate the whole area of the peak or the peak area may be approximated by using the width of the peak at baseline. Most commonly, this will be done through the use of a standard integrator, of which there are many commercial versions. However, other methods such as physically cutting out the peak and weighing the paper, or manually measuring the width of the peak at baseline, may be used as a relative measure of the area under the curve.

It is understood that the water dip is generally a negative peak, resulting from the lower detector response of the water from the sample injection from the bulk electrolyte, while the sample peaks are generally positive peaks, resulting from an increased detector response over the bulk electrolyte. The direction of the peak is irrelevant in the determination of the area.

By the term "normalization or standardization of variabilities between electropherograms" or grammatical equivalents herein is meant the process by which differences or variations in the way samples or standards run can be corrected. Thus, sample runs and standard runs are normalized when the experimental parameters are identical or near identical. When used in the present invention, normalization particularly means the correction or adjustment for changes in the sample injection volume and the electroosmotic flow velocity such that the EOF and sample injection volume of the standard run and the EOF and sample injection volume of the sample run are essentially the same. This results in the corresponding adjustment of the sample peaks.

By the term "system running buffer" or grammatical equivalents herein is meant the bulk buffer of the chromatography system. This is the buffer that is constantly introduced into the column or capillary. The running buffer is chosen on a variety of parameters, including compatibility with the sample, with the column or capillary, and the method of detection to be utilized. It may be an electrolyte, particularly in the case of conductometric CE. It may be a buffer containing fluorescent markers or high absorbtivity, in the cases of indirect fluorescence detection and indirect photometric detection, respectively.

DETAILED DESCRIPTION OF THE INVENTION

The present invention relates to a method for the standardization and normalization of chromatograms, and in particular electropherograms of CE. The present invention allows the normalization of variabilities present in chromatograms between standard and sample CE runs.

In one embodiment, the present invention relates to the normalization of variabilities associated with differences in injection volumes of samples. A standard is injected and the area of the water dip and of the standard is determined. A sample is then injected and the area of the water dip and of the sample is determined. The peak area of the sample peak is adjusted by use of the formula:

$$\text{Adjusted Peak Area} = (\text{measured peak area})(\text{Area}_{wd}\ std/\text{Area}_{wd}\ sample) \quad (1)$$

wherein
$\text{Area}_{wd}\ std$ = the area of the water dip in the standard run;
$\text{Area}_{wd}\ sample$ = area of the water dip in the sample run.

After the adjusted peak areas are calculated, the concentrations of the samples are calculated by the use of the formula:

$$\text{Sample concentration} = (\text{sample adjusted peak area})(\text{standard concentration}/\text{standard peak area}). \quad (2)$$

The sample concentration is thus in the units of the standard concentration.

In another preferred embodiment, the present invention relates to the normalization of variabilities associated with differences in the flow velocity of the system running buffer. In particular, the invention relates to variabilities associated with electroosmotic flow of the bulk electrolyte within the capillary of CE. These differences may be due to a change or variability of the capillary, to adsorbed material on the wall of the capillary, or to alterations in the applied voltage, amongst other things. This is also significant if an integrator is used in the area determination of peaks, since the integration is dependent on time, and a change in the flow rate may result in a change in the area.

Variabilities in electroosmotic flow velocity may be corrected in several ways, using the following variables and equations.

Since the water in the sample volume (or standard volume) is not ionized, it moves down the capillary at the same velocity as the bulk electrolyte, as a result of the electroosmotic flow. This is expressed in equation (3):

$$v_{eo} = L/t_w \quad (3)$$

where
$v_{eo}$ = electroosmotic flow velocity in cm per second;
$L$ = the length of the capillary in cm;
$t_w$ = migration time of the water dip, in seconds.

The total migration velocity is the vector sum of the electroosmotic flow velocity and the electrophoretic velocity, expressed in (4):

$$v_{tot} = v_{eo} + v_{ep} \quad (4)$$

where
$v_{tot}$ = total migration velocity in cm/sec;
$v_{ep}$ = net electrophoretic velocity in cm/sec;
$v_{eo}$ = electroosmotic flow velocity in cm/sec.

Note that $v_{ep}$ can be either positive or negative in sign, depending on whether the sample ion is electrophoretically migrating towards the outlet electrode or away from it.

Combining (3) and (4) gives (5):

$$v_{tot} = L/t_w + v_{ep} \quad (5)$$

$v_{tot}$ can also be calculated by dividing the total migration length by the observed migration time, (6):

$$v_{tot} = L/t_s \quad (6)$$

where
$t_s$ = observed migration time for sample ion in seconds.

Combining (5) and (6) gives (7):

$$v_{ep} = L(1/t_s - 1/t_w)$$

Rearrangement gives (8):

$$v_{ep}/L = 1/t_s - 1/t_w \quad (8)$$

If L is not changed, the electrophoretic index $v_{ep}/L$, or E, electrophoretic velocity per unit length may be used as the identifying index that is independent of $v_{eo}$.

$$E = 1/t_s - 1/t_w \quad (9)$$

where
$E = v_{ep}/L$ = electrophoretic index.

If, however, either the length of capillary or the voltage is varied between calibration conditions and the sample conditions, then electrophoretic mobility is used. Electrophoretic mobility is the electrophoretic velocity per unit field strength, (10):

$$u_{ep} = v_{ep}/(V/L) = v_{ep}L/V \quad (10)$$

where
$u_{ep}$ = electrophoretic mobility in cm$^2$/volt sec;
$V$ = total applied voltage, in volts.

Combining (8) and (9) gives (10):

$$U_{ep} = L^2(1/t_s - 1/t_w)/V \quad (10)$$

Thus the electrophoretic mobility, $u_{ep}$, can be calculated from observed values of $t_s$ and $t_w$, and values of L and V which are known.

In another embodiment, a method is described for the normalization of variabilities associated with changes in the flow velocity of the system running buffer in chromatography systems.

In a preferred embodiment, the value chosen as the migration time of any particular peak is the minima or maxima of the peak, depending on whether the peak is negative or positive. That is, for the determination of the migration time of a water dip peak, the minima of the conductance peak is chosen as the migration time. For a sample or standard peak, the maxima of the conductance peak is chosen. Alternative embodiments may use the beginning of the peak or the end of the peak, so long as the same parameter is used consistently.

In a preferred embodiment, the sample and standard are 100% aqueous. In alternative embodiments, the sample and standard are equal in composition if another solvent is present.

In a preferred embodiment, the present invention may be used in the generation of a standard calibration curve. Multiple injections of standards at different concentrations are made. Using one run as the reference, the observed area responses from all other injections of standards are adjusted or corrected using the above techniques. Then the adjusted peak area is plotted as a function of concentration. This is multi-point calibration with the use of the water dip for corrections in any variation during calibration.

The present invention will find use in any chromatography system which utilizes a detector capable of reporting a change in the detector output as a result of a difference between the sample diluent and the system running buffer. In a preferred embodiment, the detection is conductivity detection, suppressed conductivity detection, direct or indirect photometric detection, or direct or indirect fluorescence detection.

Having described the particular methods employed in the present invention for the normalization and standardization of CE electropherograms, and detailing how these methods may be utilized, and showing the successful normalization of CE electropherograms, the present disclosure is sufficient to enable one skilled in the art to use this knowledge to produce the end results by equivalent means using generally available techniques.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1: Correction of Electroosmotic Flow Rate in a Suppressed Conductometric CE System The system described below is significantly the same as is disclosed in U.S. Pat. No. 5,296,115.
Capillary: 75 μm i.d., 60 cm long fused silica
Electrolyte: 2 mm Sodium Borate
Voltage: pos. 24KV
Injection: Hydrostatic—30 mm, 10 sec.
Supressor Regenerate: 10 mM Sulfuric Acid To generate FIG. 2, which depicts a standard CE electropherogram, 10 μM each of the following compounds was injected:
1. carbonate
2. chlorite
3. fluoride
4. phosphate
5. chlorate
6. perchlorate
7. nitrate
8. nitrite
9. sulfate
10. chloride
11. bromide
12. chromate Next, peaks 5–8, corresponding to chlorate, perchlorate, nitrate and nitrite were chosen for further study because they were well resolved. Each of the sample runs utilized the same conditions as above. The results are shown in table 1.

TABLE 1

TABLE OF RAW AND WATER DIP CORRECTED DATA FROM SUPPRESSED CE SYSTEM

| Sample | Mtwd | Mt1 | Mt2 | Mt3 | Mt4 | Mt1corr | Mt2corr | Mt3corr | Mt4corr |
|---|---|---|---|---|---|---|---|---|---|
| Std Run | 2.480 | 7.570 | 8.480 | 10.120 | 11.000 | −13.556 | −14.265 | −15.221 | −15.616 |
| Run 1 | 2.460 | 7.480 | 8.380 | 9.970 | 10.850 | −13.641 | −14.359 | −15.310 | −15.717 |
| Run 2 | 2.490 | 7.470 | 8.380 | 10.030 | 10.950 | −13.387 | −14.114 | −15.095 | −15.514 |
| Run 3 | 2.500 | 7.770 | 8.750 | 10.500 | 11.470 | −13.565 | −14.286 | −15.238 | −15.641 |
| Run 4 | 2.480 | 7.800 | 8.770 | 10.540 | 11.470 | −13.751 | −14.460 | −15.417 | −15.802 |
| Run 5 | 2.490 | 7.730 | 8.690 | 10.390 | 11.340 | −13.612 | −14.327 | −15.268 | −15.671 |
| Run 6 | 2.480 | 7.750 | 8.700 | 10.420 | 11.370 | −13.710 | −14.414 | −15.363 | −15.764 |
| Run 7 | 2.500 | 7.900 | 8.900 | 10.670 | 11.670 | −13.671 | −14.382 | −15.314 | −15.716 |
| Run 8 | 2.480 | 7.830 | 8.850 | 10.650 | 11.630 | −13.776 | −14.512 | −15.466 | −15.862 |
| Run 9 | 2.480 | 7.950 | 9.020 | 10.920 | 12.000 | −13.872 | −14.618 | −15.583 | −15.995 |
| Run 10 | 3.020 | 15.270 | 18.980 | 23.530 | | −13.282 | −13.922 | −14.431 | |
| Run 11 | 2.520 | 8.050 | 9.180 | 11.280 | 12.520 | −13.630 | −14.395 | −15.409 | −15.848 |
| Run 12 | 2.580 | 8.970 | 10.370 | 13.200 | 15.000 | −13.806 | −14.558 | −15.592 | −16.047 |
| Run 13 | 2.670 | 9.880 | 11.500 | 14.630 | 16.600 | −13.666 | −14.379 | −15.309 | −15.715 |
| Run 14 | 2.670 | 9.920 | 11.570 | 14.930 | 17.200 | −13.686 | −14.405 | −15.378 | −15.820 |
| Run 15 | 2.880 | 14.320 | 18.080 | 23.800 | | −13.869 | −14.596 | −15.260 | |
| Average | 2.570 | 8.980 | 10.410 | 12.850 | 12.510 | −13.655 | −14.374 | −15.291 | −15.766 |
| Std Dev | 0.163 | 2.403 | 3.329 | 4.501 | 2.130 | 0.158 | 0.176 | 0.263 | 0.144 |
| RSD | 6.324 | 26.763 | 31.982 | 35.027 | 17.024 | −1.159 | −1.227 | −1.719 | −0.913 |

| Sample | U1 | U2 | U3 | U4 |
|---|---|---|---|---|
| Std Run | −1.085E-06 | −1.141E-06 | −1.218E-06 | −1.249E-06 |
| Run 1 | −1.091E-06 | −1.149E-06 | −1.225E-06 | −1.257E-06 |
| Run 2 | −1.071E-06 | −1.129E-06 | −1.208E-06 | −1.241E-06 |
| Run 3 | −1.085E-06 | −1.143E-06 | −1.219E-06 | −1.251E-06 |
| Run 4 | −1.100E-06 | −1.157E-06 | −1.233E-06 | −1.264E-06 |
| Run 5 | −1.089E-06 | −1.146E-06 | −1.221E-06 | −1.254E-06 |
| Run 6 | −1.097E-06 | −1.153E-06 | −1.229E-06 | −1.261E-06 |
| Run 7 | −1.094E-06 | −1.151E-06 | −1.225E-06 | −1.257E-06 |
| Run 8 | −1.102E-06 | −1.161E-06 | −1.237E-06 | −1.269E-06 |
| Run 9 | −1.110E-06 | −1.169E-06 | −1.247E-06 | −1.280E-06 |
| Run 10 | −1.063E-06 | −1.114E-06 | −1.155E-06 | Mt too long |
| Run 11 | −1.090E-06 | −1.152E-06 | −1.233E-06 | −1.268E-06 |
| Run 12 | −1.104E-06 | −1.165E-06 | −1.247E-06 | −1.284E-06 |

TABLE 1-continued
TABLE OF RAW AND WATER DIP CORRECTED DATA FROM SUPPRESSED CE SYSTEM

|  |  |  |  |  |
|---|---|---|---|---|
| Run 13 | −1.093E-06 | −1.150E-06 | −1.225E-06 | −1.257E-06 |
| Run 14 | −1.095E-06 | −1.152E-06 | −1.230E-06 | −1.266E-06 |
| Run 15 | −1.110E-06 | −1.168E-06 | −1.221E-06 | Mt too long |
| Average | −1.092E-06 | −1.150E-06 | −1.223E-06 | −1.261E-06 |
| Std Dev | 1.266E-08 | 1.410E-08 | 2.103E-08 | 1.151E-08 |
| RSD | −1.159 | −1.227 | −1.719 | −0.913 |

Mt wd is the migration time for the water dip, Mt1–Mt4 represent the migration time for peaks 5-8. Mt1 corr–Mt corr represent the calculated electrophoretic velocity, vep, where $vep = L(1/ts - 1/tw)$. U1–U4 is the electrophoretic mobility, $u_{ep} = vepL/V$. The RSD for Mt for the raw data was significantly larger than the RSD for Mt corr, indicating the normalizing effect of the calculation for changes in EO flow. Also, the standard deviation of U1–U4 was well within the difference between the electrophoretic mobilities; thus, $u_{ep}$ may be used to identify the compounds.

Example 2: Correction of Electroosmotic Flow Rate in a CE System Utilizing Indirect Photometric Detection Capillary: #1–#3 75 μm i.d., 50 cm long fused silica
Electrolyte: 5.0 mM potassium acid phthalate, 0.5 mM tetradecyl trimethyl ammonium bromide (TTAB), 2.0 mM sodium borate, pH 5.9
Voltage: neg. 15 KV
Injection: gravity, 100 mm for 2 sec.
supressor regenerant: 10 mN sulfuric acid Three different capillaries were utilized. Two standards, 2 ppm fluoride and 15 ppm phosphate, were utilized in the standard run. As is shown in Table 2, Mt1 and Mt2 are the retention times for the standards. Mt1 corr and Mt2 corr represent the calculated electrophoretic velocity, vep, where $vep = L(1/ts - 1/tw)$. U1 and U2 is the electrophoretic mobility, $u_{ep} = vepL/V$. As is shown by the data in Table 2, this method allows standardization even if different capillaries is used.

TABLE 2
TABLE OF RAW AND WATER DIP CORRECTED DATA FROM INDIRECT PHOTOMETRIC CE SYSTEM

| Sample | Capillary | Mtwd | Mt1 | Mt2 | Mt1corr | Mt2corr | U1 | U2 |
|---|---|---|---|---|---|---|---|---|
| Std Run | 1 | 8.100 | 2.830 | 3.680 | 11.495 | 7.414 | 9.196E-07 | 5.931E-07 |
| Run 1 | 1 | 8.070 | 2.830 | 3.680 | 11.472 | 7.391 | 9.178E-07 | 5.913E-07 |
| Run 2 | 1 | 8.020 | 2.830 | 3.670 | 11.433 | 7.390 | 9.147E-07 | 5.912E-07 |
| Run 3 | 2 | 8.090 | 2.850 | 3.700 | 11.363 | 7.333 | 9.091E-07 | 5.866E-07 |
| Run 4 | 2 | 8.050 | 2.850 | 3.690 | 11.333 | 7.339 | 9.066E-07 | 5.871E-07 |
| Run 5 | 2 | 8.010 | 2.840 | 3.690 | 11.363 | 7.308 | 9.091E-07 | 5.846E-07 |
| Run 6 | 3 | 8.350 | 2.930 | 3.810 | 11.077 | 7.135 | 8.861E-07 | 5.708E-07 |
| Run 7 | 3 | 8.490 | 2.880 | 3.750 | 11.472 | 7.444 | 9.177E-07 | 5.955E-07 |
| Run 8 | 3 | 8.130 | 2.870 | 3.720 | 11.272 | 7.291 | 9.017E-07 | 5.833E-07 |
| Average | NA | 8.150 | 2.860 | 3.710 | 11.364 | 7.338 | 9.092E-07 | 5.871E-07 |
| Std Dev | NA | 0.164 | 0.033 | 0.045 | 0.131 | 0.091 | 1.048E-08 | 7.308E-09 |
| RSD | NA | 2.011 | 1.146 | 1.205 | 1.153 | 1.245 | 1.153 | 1.245 |

Example 3: Correlation of sample volume with water dip volume

Figure 1:
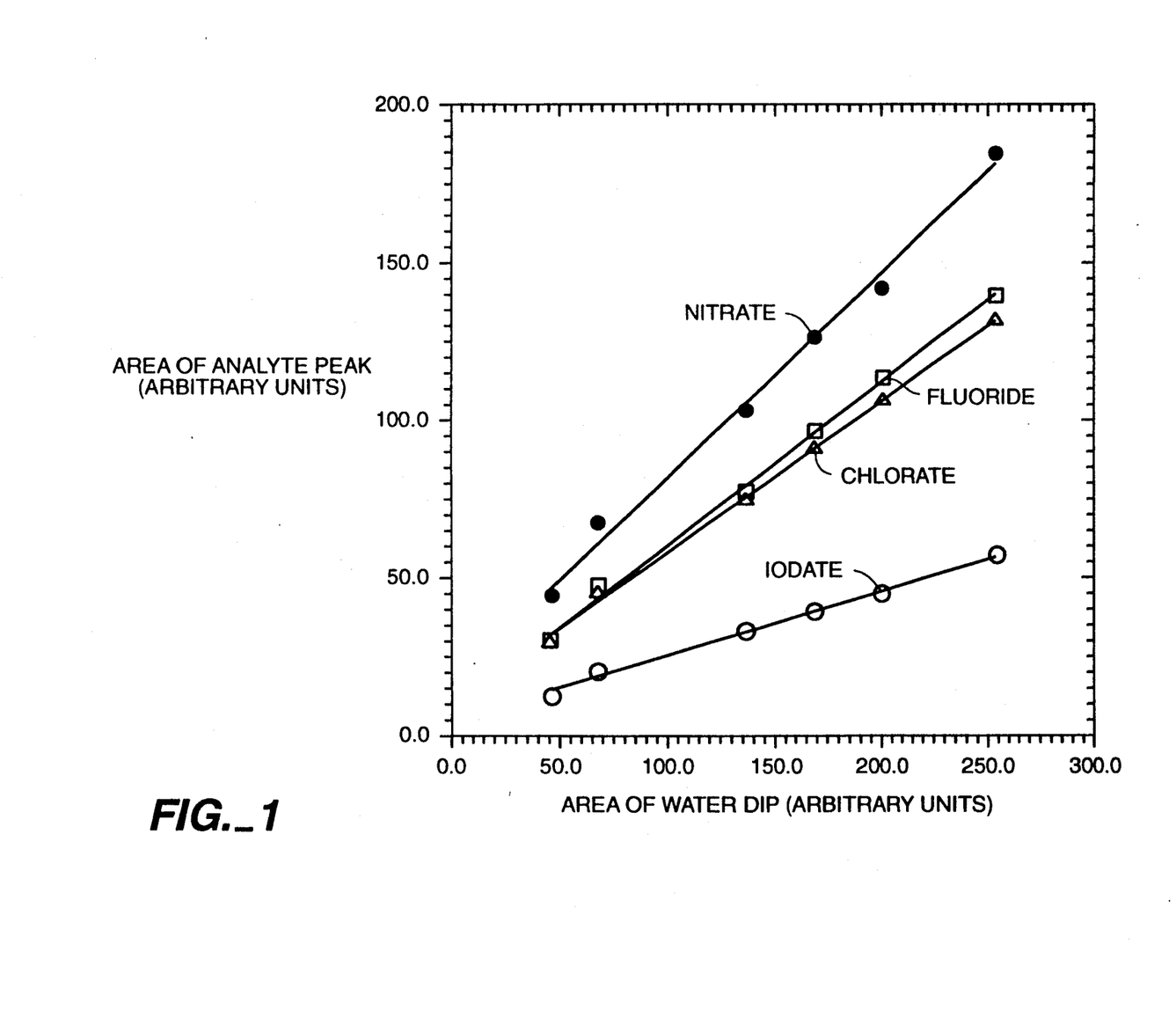
FIG. 1 depicts the linear relationship between the area of the water dip and the analyte peak area. Note that extrapolation results in a common intersection point for these best fit lines, within experimental error.

The system of example 1 was run, except that the sample volume injected was deliberately varied. This was run using four separate analyte peaks, namely iodate, fluoride, chlorate and nitrate. The plot of the area of the water dip versus the plot of the analyte peak is seen in FIG. 1.

This example illustrates the correlation of the size or area of the water dip with the size or area of the sample peaks.

Example 4: Correction of Sample Injection Volumes

A chromatography system or CE system may be run as described in examples 1 and 2 or using any other common chromatography system, as long as the system enables the generation of a chromatogram or electropherogram. Perferably the detector used is operably connected to an integrator or other data collection device, but this is not necessary.

The concentration of the analyte peaks may be calculated as follows. First, a standard or set of standards of known concentration are run, and then at least one run of samples of unknown concentration are run. Then the adjusted peak area of the first sample peak is calculated according to the equation:

$$\text{adjusted peak area} = (\text{measured peak area})(\text{Area}_{wd\ std}/\text{Area}_{wd\ sample})$$

Then, the sample concentration is calculated using the formula:

$$\text{sample concentration} = (\text{sample adjusted peak area})(\text{standard concentration}/\text{standard peak area})$$

This may be repeated for as many sample peaks as necessary.

Alternatively, the peak width of the water dip at baseline, in seconds, may be used to correct the sample peak concentration.

We claim:

1. A method of normalizing variabilities between chromatograms of standard and sample chromatography runs, said variabilities associated with sample injection, said variabilities resulting from differences in the sample injection volume that alter the sample chromatograms, said method comprising the steps of:
    (1) creating a chromatogram of at least one standard of known concentration, and at least one chromatogram for a sample of unknown concentration, said chromatograms being generated utilizing a detection method which results in a change in the detector output as a result of a difference between the sample diluent and the system running buffer;

(2) determining for each said chromatogram an area of the water dip peak, the standard peaks and the sample peaks;

(3) using the relationship between the area of the water dip of the standard run and the area of the water dip of the sample run to correlate the sample concentration with the standard concentration.

2. The method of claim 1 wherein said detection method is selected from the group consisting of conductometric detection, suppressed conductometric detection, direct or indirect photometric detection, and direct or indirect fluorescence detection.

3. The method of claim 1 wherein said chromatograms are capillary electrophoresis electropherograms.

4. A method of normalizing variabilities between chromatograms of standard and sample chromatography runs, said variabilities associated with sample injection, said variabilities resulting from differences in the sample injection volume that alter the sample chromatograms, the method comprising the steps of:

(1) creating a chromatogram of at least one standard of known concentration, and at least one chromatogram of a sample of unknown concentration, said chromatograms being generated utilizing a detection method which results in a change in the detector output as a result of a difference between the sample diluent and the system electrolyte;

(2) determining for each said chromatogram an area of the water dip peak, the standard peaks and the sample peaks;

(3) calculating adjusted peak areas for said sample peaks and said sample run water dip according to the formula:

Adjusted Peak Area=(measured peak area)(Area$_{wd\ std}$/Area$_{wd\ sample}$);

wherein

Area$_{wd\ std}$=the area of the water dip in the standard run;

Area$_{wd\ sample}$=area of the water dip in the sample run; and (4) determining sample concentration according to the formula:

Sample concentration=(sample adjusted peak area)(standard concentration/standard peak area).

5. The method of claim 4 wherein said detection method is selected from the group comprising conductometric detection, suppressed conductometric detection, direct or indirect photometric detection, and direct or indirect fluorescence detection.

6. The method of claim 4 wherein said chromatograms are capillary electrophoresis electropherograms.

7. A method of normalizing variabilities between chromatograms of standard and sample chromatography runs, said variabilities associated with changes in the flow velocity of the system electrolyte, said variabilities resulting in differences in the migration times of samples and standards, the method comprising the steps of:

(1) creating a chromatogram of at least one standard, and at least one chromatogram of samples of interest, said chromatograms being generated utilizing a detection method which results in a change in the detector output as a result of a difference between the sample diluent and the system running buffer;

(2) determining a migration time of the water dip, the standards and the samples in the standard and sample runs;

(3) calculating adjusted peak migration times according to the formula:

adjusted migration time=(measured migration time)(migration time$_{wd\ std}$/migration time$_{wd\ sample}$);

wherein migration time$_{wd\ std}$=the migration time of the water dip in the standard run;

migration time$_{wd\ sample}$=the migration time of the water dip in the sample run; and (4) identifying sample peaks by adjusted migration time by correlating the adjusted migration times of the samples to the adjusted migration times of the standards.

8. The method of claim 7 wherein said detection means is selected from the group consisting of conductometric detection, suppressed conductometric detection, direct or indirect photometric detection, and direct or indirect fluorescence detection.

9. A method of normalizing variabilities between electropherograms of standard and sample capillary electrophoresis runs, said variabilities associated with changes in the electroosmotic flow velocity of capillary electrophoresis, said variabilities resulting in differences in the migration times of samples and standards, the method comprising the steps of:

(1) creating an electropherogram of at least one standard, and at least one electropherogram of samples of interest, said electropherograms being generated utilizing a detection method which results in a change in the detector output as a result of a difference between the sample diluent and the system electrolyte;

(2) determining a migration time of the water dip, the standards and the samples in the standard and sample runs;

(3) calculating the electrophoretic mobility of each of the standards and samples according to the formula:

$$u_{ep}=L^2(1/t_s-1/t_w)/V$$

wherein $u_{ep}$=electrophoretic mobility;

L=length of capillary;

V=applied voltage;

$t_w$=migration time of the water dip;

$t_s$=migration time of the sample; and (4) identifying sample peaks by electrophoretic mobility by correlating the electrophoretic mobility of the samples to the electrophoretic mobility of the standards.

10. The method of claim 9 wherein said detection method is selected from the group comprising conductometric conduction, suppressed conductometric detection, direct or indirect photometric detection, and direct or indirect fluorescence detection.

11. A method of normalizing variabilities between electropherograms of standard and sample capillary electrophoresis runs wherein the applied voltage and the capillary have not been altered, said variabilities associated with changes in the electroosmotic flow velocity of capillary electrophoresis, said variabilities resulting in differences in the migration times of samples and standards, said method comprising the steps of:

(1) creating an electropherogram of at least one standard, and at least one electropherogram of a sample of interest, said electropherograms being generated utilizing a detection method which results in a change in the detector output as a result of a difference between the sample diluent and the system electrolyte;

(2) determining the migration time of the water dips, the standards and the samples, in the standard and sample runs;

(3) calculating the electrophoretic index of each of the standards and samples according to the formula:

$$E = 1/t_s - 1/t_w$$

wherein
E = the electrophoretic index;
$t_w$ = migration time of the water dip;
$t_2$ = migration time of the sample; and (4) identifying sample peaks by electrophoretic index by correlating electrophoretic index of samples to the electrophoretic index of standards.

12. The method of claim 11 wherein said detection means is selected from the group consisting of conductometric detection, suppressed conductometric detection, direct or indirect photometric detection, and direct or indirect fluoroscence detection.

13. The method of claim 4 further comprising the steps of:

(1) determining the migration time of the water dip, the standards and the samples in the standard and sample runs;

(2) calculating the electrophoretic mobility of each of the standards and samples according to the formula:

$$u_{ep} = L^2(1/t_s - 1/t_w)/V$$

wherein
$u_{ep}$ = electrophoretic mobility;
L = length of capillary;
V = applied voltage;
$t_w$ = migration time of the water dip;
$t_s$ = migration time of the sample; and (3) identifying sample peaks by electrophoretic mobility by correlating the electrophoretic mobility of the samples to the electrophoretic mobility of the standards.

14. The method of claim 13 wherein said detection means is selected from the group consisting of conductometric detection, suppressed conductometric detection, direct or indirect fluorescence detection and direct or indirect photometric detection.

15. The method of claim 4, wherein the applied voltage and the capillary have not been altered, said method further comprising the steps of:

(1) determining the migration time of the water dips, the standards and the samples, in the standard and sample runs;

(2) calculating the electrophoretic index of each of the standards and samples according to the formula:

$$E = 1/t_s - 1/t_w$$

wherein
E = the electrophoretic index;
$t_w$ = migration time of the water dip;
$t_s$ = migration time of the sample; and (3) identifying sample peaks by electrophoretic index by correlating electrophoretic index of samples to the electrophoretic index of standards.

16. An apparatus for the normalization and standardization of variabilities between chromatograms of standard and sample chromatography runs, said variabilities associated with sample injection, said variabilities resulting from differences in the sample injection volume that alter the sample chromatograms, said apparatus comprising (1) chromatography separating means for separating sample compounds;

(2) detection means for producing a chromatogram with peaks, said detection means capable of reporting a change in the detector output as a result of a difference between the sample diluent and the system running buffer;

(3) integration means, operably coupled to the detection means, for calculating an area of the water dip peaks, the sample peaks and the standard peaks associated with said chromatogram;

(4) analysis means, operably coupled to Said integration means, for determining a relationship between said calculated area of the water dip of said standard run and said calculated area of the water dip of said sample run, such that the concentration of said sample may be correlated to the concentration of said standard.

17. The method of claim 16 wherein said detection means is selected from the group consisting of conductometric detection, suppressed conductometric detection, direct or indirect photometric detection and direct or indirect fluorescence detection.

18. The apparatus according to claim 16 wherein said analysis means includes:

(1) means for calculating the adjusted peak areas of the sample peaks and the sample run water dip according to the formula:

Adjusted Peak Area = (measured peak area)(Area$_{wd\ std}$/Area$_{wd\ sample}$);

wherein
Area$_{wd\ std}$ = the area of the water dip in the standard run;
Area$_{wd\ sample}$ = area of the water dip in the sample run; and (2) means for determining the sample concentration according to the formula:

Sample concentration = (sample adjusted peak area)(standard concentration/standard peak area).

19. The apparatus according to claim 16 wherein said analysis means includes:

(1) means for calculating the adjusted migration times of the sample peaks and the sample run water dip according to the formula:

adjusted migration time = (measured migration time)(migration time$_{wd\ std}$/migration time$_{wd\ sample}$);

wherein migration time$_{wd\ std}$ = the migration time of the water dip in the standard run;

migration time$_{wd\ sample}$ = the migration time of the water dip in the sample run.

20. An apparatus for the normalization and standardization of variabilities between electropherograms of standard and sample capillary electrophoresis runs, said variabilities resulting from changes in the electroosmotic flow velocity of capillary electrophoresis runs, said apparatus comprising
   (1) capillary electrophoresis separating means for separating sample compounds;
   (2) detection means for producing an electropherogram with peaks, said detection means capable of reporting a change in the detector output as a result of a difference between the sample diluent and the system running buffer;
   (3) timing means, operably coupled to said detection means, for determining migration time of the water dip peaks, standard peaks and sample peaks associated with said electropherograms;
   (4) analysis means, operably coupled to said timing means, for correlating electrophoretic mobility of said sample peaks to migration time to migration time of the water dip of the standard run and the migration time of the water dip of the sample run.

21. The apparatus according to claim 20 wherein said analysis means includes means for calculating the electrophoretic mobility of each standard and sample according to the formula:

$$u_{ep} = L^2(1/t_s 1 - 1/t_w)/V$$

wherein
   $u_{ep}$ = electrophoretic mobility;
   L = length of capillary;
   V = applied voltage;
   $t_w$ = migration time of the water dip;
   $t_s$ = migration time of the sample.

22. The apparatus of claim 20 wherein said detection means is selected from the group consisting of conductometric detection, suppressed conductometric detection, direct or indirect photometric detection, and direct or indirect fluorescence detection.

23. The apparatus according to claim 16 wherein said analysis means includes means for calculating the electrophoretic index of each standard and sample according to the formula:

$$E = 1/t_s - 1/t_w$$

wherein
   E = the electrophoretic index;

$t_w$ = migration time of the water dip;
$t_s$ = migration time of the sample.

24. The apparatus of claim 16, wherein said variabilities further result from changes in electroosmotic flow velocity, further including:
   (1) timing means for determining migration time of the water dip peaks, the standard peaks and the sample peaks; and
   (2) analysis means, operably coupled to said timing means, for determining a relationship between electrophoretic mobility of the standard peaks and the electrophoretic mobility of the sample peaks, based on a relationship of the migration time of the water dip of the standard run and the migration time of the water dip of the sample run.

25. The apparatus of claim 24, wherein said analysis means includes:
   (1) means for calculating adjusted peak areas of the sample peaks and the sample run water dip according to the formula:

Adjusted Peak Area = (measured peak area)(Area$_{wd\ std}$/Area$_{ws\ sample}$);

wherein
   Area$_{wd\ std}$ = the area of the water dip in the standard run;
   Area$_{wd\ sample}$ = area of the water dip in the sample run; and (2) means for determining sample concentration according to the formula:

Sample concentration = (sample adjusted peak area)(standard concentration/standard peak area); and (3) means for calculating electrophoretic mobility of each of the standards and samples according to the formula:

$$u_{ep} = L^2(1/t_s - 1/t_w)/V$$

wherein
   $u_{ep}$ = electrophoretic mobility;
   L = length of capillary;
   V = applied voltage;
   $t_w$ = migration time of the water dip;
   $t_s$ = migration time of the sample.

26. The apparatus of claim 25 wherein said detection means is selected from the group consisting of conductometric detection, suppressed conductometric detection, indirect photometric detection and indirect fluorescence detection.

* * * * *